US00PP24211P2

(12) United States Plant Patent
Hofmann

(10) Patent No.: US PP24,211 P2
(45) Date of Patent: Feb. 4, 2014

(54) ***LOBULARIA* PLANT NAMED 'INLBUSNOWHI'**

(50) Latin Name: *Lobularia maritima*
Varietal Denomination: Inlbusnowhi

(75) Inventor: Birgit Hofmann, Rüdesheim am Rhein (DE)

(73) Assignee: Innova Plant GmbH & Co. KG, Gensingen (DE)

( * ) Notice: Subject to any disclaimer, the term of this patent is extended or adjusted under 35 U.S.C. 154(b) by 86 days.

(21) Appl. No.: 13/385,061

(22) Filed: Jan. 31, 2012

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

A new cultivar of *Lobularia* plant named 'Inlbusnowhi' that is characterized by a compact rounded and mounding habit and small white flowers with lilac colored sepals.

1 Drawing Sheet

Botanical classification: *Lobularia maritima.*
Variety denomination: 'Inlbusnowhi'.

BACKGROUND OF THE INVENTION

The present invention relates to a new and distinct cultivar of *Lobularia* plant botanically known as *Lobularia maritima* and hereinafter referred to by the cultivar name 'Inlbusnowhi'.

The new *Lobularia* is the product of a planned breeding program conducted by the inventor in Gensingen, Germany. The objective of the breeding program is to create new *Lobularia* cultivars with compact habits and unique flower colors.

'Inlbusnowhi' originated from a crossing in the Summer of 2009 of the female or seed parent *Lobularia* 'Inlbusnopr' (U.S. Plant Pat. No. 21,594) and the male or pollen parent *Lobularia* 'Inlbusnopr' (U.S. Plant Pat. No. 21,594). *Lobularia* 'Inlbusnopr' is a crossing of a *Lobularia canariensis* as the female, or seed parent and a *Lobularia muritime* as the male or pollen parent and is heterozygous. The self-crossing was performed to produce a range of plants with intermediate types. The resulting seeds were subsequently planted and grown. The cultivar 'Inlbusnowhi' was selected by the inventor in the Fall of 2009 as a single plant within the progeny of the stated cross in Gensingen, Germany.

Asexual reproduction of the new cultivar 'Inlbusnowhi' first occurred by terminal cuttings in the Fall of 2009 in Gensingen, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Lobularia* cultivar 'Inlbusnowhi'. These traits in combination distinguish 'Inlbusnowhi' as a new and distinct cultivar apart from other existing known varieties of *Lobularia.*

1. *Lobularia* 'Inlbusnowhi' exhibits a compact rounded and mounding habit.

2. *Lobularia* 'Inlbusnowhi' exhibits small white flowers with lilac colored sepals.

The closest comparison cultivar is the parent plant *Lobularia* 'Inlbusnopr'. 'Inlbusnowhi' is distinguishable from 'Inlbusnopr' by the following characteristics:

1. 'Inlbusnowhi' exhibits a more rounded and mounding habit.
2. 'Inlbusnowhi' has smaller flowers.
3. 'Inlbusnowhi' has lilac sepals. The sepals of 'Inlbusnopr' are green.

'Inlbusnowhi' can be compared to *Lobularia* 'White Stream' (not patented). 'Inlbusnowhi' is distinguishable from 'White Stream' by the following characteristics:

1. 'Inlbusnowhi' exhibits a larger overall size than the overall size of 'White Stream'.
2. 'Inlbusnowhi' has larger flowers than the flowers of 'White Stream'.
3. 'Inlbusnowhi' exhibits a more rounded and mounding habit than 'White Stream'.

BRIEF DESCRIPTION OF THE DRAWING

The accompanying photograph illustrates the distinguishing traits of *Lobularia* 'Inlbusnowhi'. The plant in the photograph shows an overall view of a 3 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Lobularia* cultivar named 'Inlbusnowhi'. Data was collected in Gensingen, Germany from 3 month old glass greenhouse grown plants in 14 cm. diameter containers. The time of year was Winter and the temperature range was 12-14 degrees Centigrade during the day and 10-12 degrees Centigrade at night. The light level was 3000 lux for 14 hours per day. No growth retardants were used. Color determinations are in accordance with The Royal Horticultural Society Colour Chart 2007 edition, except where general color terms of ordinary dictionary significance are used. The growing requirements are similar to the species. 'Inlbusnowhi' has not been tested under all possible conditions and phenotypic differences may be observed with variations in environmental, climatic, and cultural conditions, however, without any variance in genotype.

Botanical classification: *Lobularia maritima* 'Inlbusnowhi'.

Annual or perennial: Annual.

Parentage: 'Inlbusnowhi' is the product of the female or seed parent *Lobularia* 'Inlbusnopr' and the male or pollen parent *Lobularia* 'Inlbusnopr'.

Vigor: Moderate.

Growth habit: Mounding.

Plant shape: Rounded.

Suitable container size: 12-14 cm.

Height: 6 cm. in height.

Diameter: 20 cm. in diameter.

Low temperature tolerance: −2° Centigrade.

High temperature tolerance: 45° Centigrade.

Propagation: Terminal cuttings.

Time to initiate roots in summer: 12 days to initiate roots at 25° Centigrade.

Time to initiate roots in winter: 15 days to initiate roots at 20° Centigrade.

Time to produce a rooted cutting or liner in summer: 12 days at 25° Centigrade.

Time to produce a rooted cutting or liner in winter: 15 days at 20° Centigrade.

Crop time: Approximately 10 weeks.

Root system: Fine and fibrous.

Stem:

- *Branching habit*.—Freely branching.
- *Basal branching*.—Yes.
- *Average number of lateral branches*.—20.
- *Pinching*.—No.
- *Lateral branch dimensions*.—4 mm. in diameter and 14 cm. in length.
- *Internode length*.—5 mm.
- *Stem texture*.—Smooth.
- *Stem strength*.—Strong.
- *Stem color*.—144A.
- *Pubescence*.—Absent.

Foliage:

- *Leaf arrangement*.—Alternate.
- *Compound or single*.—Single.
- *Number of leaves per lateral branch*.—40.
- *Leaf shape*.—Elliptic.
- *Leaf apex*.—Acute.
- *Leaf base*.—Attenuate.
- *Leaf dimensions*.—6 cm. in length and 1 cm. in width.
- *Texture*.—Glabrous on both surfaces.
- *Pubescence*.—None.
- *Leaf margin*.—Entire.
- *Venation pattern*.—Pinnate.
- *Young leaf color* (*upper surface*).—N137B.
- *Young leaf color* (*lower surface*).—138A.
- *Mature leaf color* (*upper surface*).—N137A.
- *Mature leaf color* (*lower surface*).—138A.
- *Vein color* (*upper surface*).—144A.
- *Vein color* (*under surface*).—144A.
- *Petiole dimensions*.—1 cm. in length and 2 mm. in diameter.
- *Petiole color*.—144A.
- *Durability of foliage to stress*.—Moderate.

Flower:

- *Inflorescence arrangement*.—Terminal cyme.
- *Inflorescence dimensions*.—2 cm. in height and 2.5 cm. in width.
- *Quantity of flowers per inflorescence*.—30 to 35.
- *Flower type*.—Single rounded flowers.
- *Quantity of flowers per lateral stem*.—300.
- *Quantity of flower buds per lateral stem*.—200.
- *Quantity of flowers and buds per plant*.—Average 3000.
- *Natural flowering season*.—April to November.
- *Time to flower*.—8 weeks.
- *Rate of flower opening*.—Every 2 days.
- *Fragrance*.—Weak honey scent.
- *Flower bud length*.—2 mm.
- *Flower bud diameter*.—1 mm. in diameter.
- *Flower bud shape*.—Ovate.
- *Bud color*.—143C.
- *Rate of bud opening*.—2 days.
- *Flower aspect*.—Outward/upright.
- *Flower shape*.—Cruciform.
- *Flower dimensions*.—8 mm. in diameter and 2 mm. in height.
- *Flower longevity*.—5-6 days.
- *Number of petals*.—4.
- *Fused or unfused*.—Unfused.
- *Petal arrangement*.—Cruciform.
- *Petal shape*.—Oval.
- *Petal texture*.—Smooth on both surfaces.
- *Petal margin*.—Entire.
- *Petal apex*.—Obtuse.
- *Petal base*.—Attenuate.
- *Petal length*.—4 mm.
- *Petal width*.—3 mm.
- *Petal color when opening* (*upper side*).—NN155D.
- *Petal color when opening* (*under side*).—NN155C.
- *Petal color fully opened* (*upper side*).—NN155D.
- *Petal color fully opened* (*under side*).—NN155C.
- *Petal color fading to*.—NN155D.
- *Self-cleaning or persistent*.—Self-cleaning.

Sepals:

- *Sepal arrangement*.—Cruciform.
- *Number of sepals*.—4.
- *Sepal shape*.—Oval.
- *Sepal margin*.—Entire.
- *Sepal apex*.—Obtuse.
- *Sepal base*.—Obtuse.
- *Sepal dimensions*.—2 mm. in length and 1 mm. in width.
- *Young sepal color* (*upper side*).—91B.
- *Young sepal color* (*under side*).—91B.
- *Mature sepal color* (*upper side*).—91B.
- *Mature sepal color* (*under side*).—91B.

Calyx:

- *Calyx shape*.—Cruciform.
- *Calyx dimensions*.—4 mm. in length and 4 mm. in diameter.

Pedicels:

- *Pedicel dimensions*.—11 mm. in length and 1 mm. in diameter.
- *Pedicel angle*.—45 degrees from stem.
- *Pedicel strength*.—Weak.
- *Pedicel color*.—137B.

Reproduction organs:

- *Stamen number*.—6.
- *Anther shape*.—Rod shaped.

*Anther size.*—2 mm.
*Anther color.*—6A.
*Amount of pollen*.—Moderate.
*Pollen color.*—6A.
*Pistil number*.—One.
*Pistil length.*—2 mm.
*Stigma shape*.—Reniform.
*Stigma color.*—149B.
*Style length.*—2 mm.
*Style color.*—149B.
*Ovary color.*—149B.

Fruit: None, sterile.

Disease and pest resistance: Disease and pest resistance has not been observed.

The invention claimed is:

1. A new and distinct variety of *Lobularia* plant named 'Inlbusnowhi' as described and illustrated.

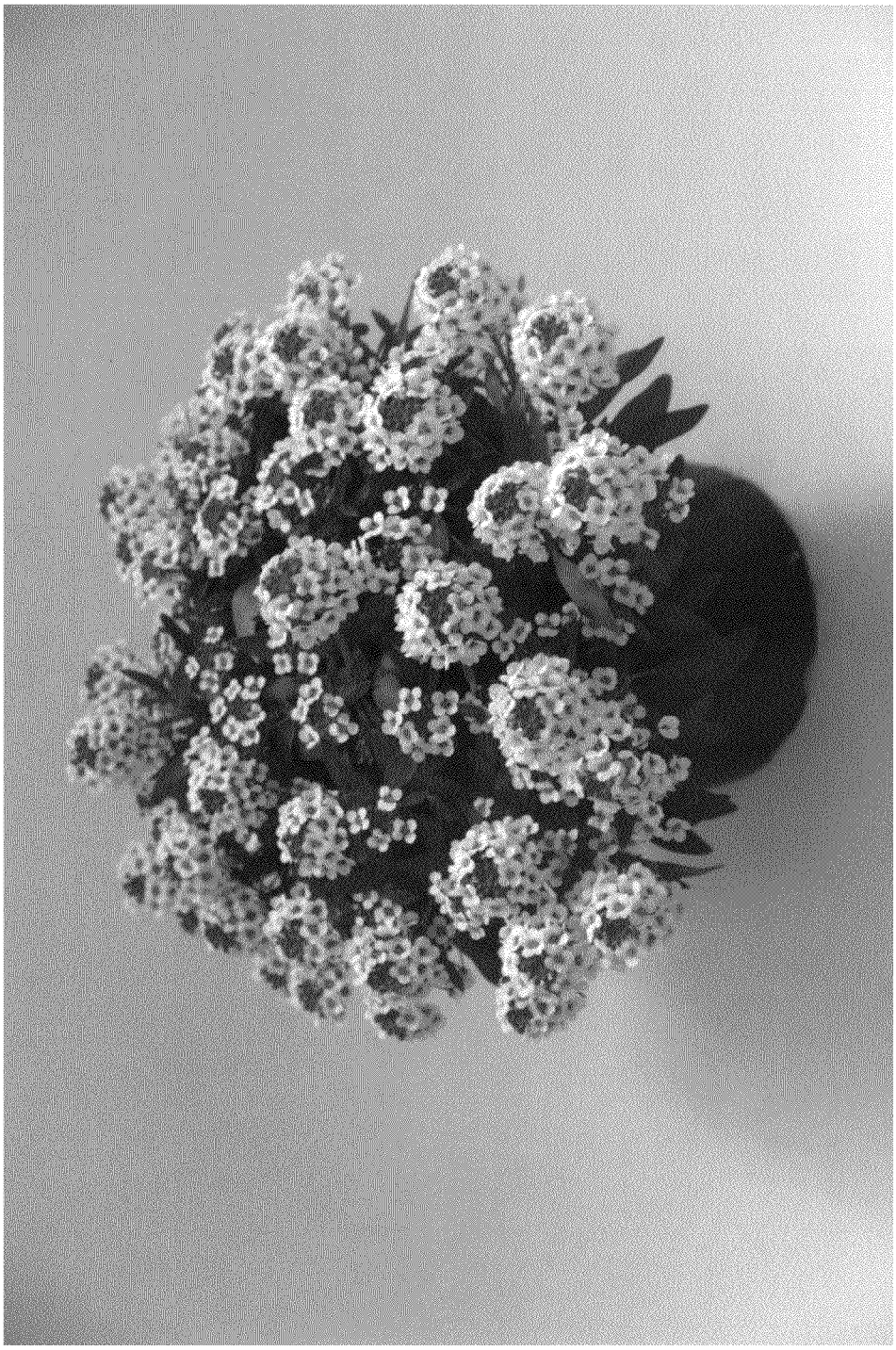

* * * * *